United States Patent

Adam et al.

Patent Number: 5,711,665
Date of Patent: Jan. 27, 1998

[54] METHOD AND APPARATUS FOR BONDING ORTHODONTIC BRACKETS TO TEETH

[75] Inventors: Randall E. Adam, Sierra Madre; Leonard A. Preston, Arcadia, both of Calif.

[73] Assignee: Minnesota Mining & Manufacturing, St. Paul, Minn.

[21] Appl. No.: 575,095

[22] Filed: Dec. 19, 1995

[51] Int. Cl.$^6$ ............................................. A61C 7/00
[52] U.S. Cl. ............................ 433/9; 433/24; 433/29
[58] Field of Search ........................ 433/9, 24, 29, 433/8

[56] References Cited

U.S. PATENT DOCUMENTS

| | | | |
|---|---|---|---|
| 3,932,940 | 1/1976 | Andreiu | 433/9 |
| 3,949,477 | 4/1976 | Cohen et al. | 433/9 |
| 4,063,360 | 12/1977 | Waller | 433/9 |
| 4,094,068 | 6/1978 | Schinhammer | 32/14 A |
| 4,216,583 | 8/1980 | Reynolds | 433/9 |
| 4,219,617 | 8/1980 | Wallshein | 433/8 |
| 4,256,455 | 3/1981 | Förster | 433/8 |
| 4,826,431 | 5/1989 | Fujimura et al. | 433/29 |
| 5,003,434 | 3/1991 | Gonser et al. | 362/32 |
| 5,049,068 | 9/1991 | Sterrett et al. | 433/9 |
| 5,098,288 | 3/1992 | Kesling | 433/9 |
| 5,110,290 | 5/1992 | Wong | 433/9 |
| 5,263,859 | 11/1993 | Kesling | 433/9 |
| 5,304,061 | 4/1994 | Nelson | 433/8 |
| 5,366,372 | 11/1994 | Hansen et al. | 433/4 |
| 5,435,720 | 7/1995 | Riebschleger | 433/9 |
| 5,607,299 | 3/1997 | Nicholson | 433/3 |

FOREIGN PATENT DOCUMENTS

| | | |
|---|---|---|
| 2106020 | 3/1995 | Canada . |
| 2139078 | 6/1995 | Canada . |
| 7-240536 | 9/1995 | Japan . |
| 2 212 010 | 7/1989 | United Kingdom . |
| WO 93/09847 | 5/1993 | WIPO . |
| WO 95/07731 | 3/1995 | WIPO . |

Primary Examiner—Cary E. O'Connor
Attorney, Agent, or Firm—Gary L. Griswold; Walter N. Kirn; James D. Christoff

[57] ABSTRACT

An orthodontic bracket includes a base with a central opening, and a body with a passage aligned with the opening. A curing light assembly includes an outer end portion that is removably received in the passage for curing adhesive beneath the central section of the bracket body. Once the adhesive beneath the central section of the bracket body has cured to temporarily tack the bracket base to the patient's tooth, adhesive extruded from the peripheral edge of the bracket base can be readily removed without dislodging the bracket from its intended position.

46 Claims, 7 Drawing Sheets

METHOD AND APPARATUS FOR BONDING ORTHODONTIC BRACKETS TO TEETH

BACKGROUND OF THE INVENTION

1. Field of the Invention

This invention broadly relates to methods and apparatus for affixing brackets used in orthodontic treatment to the surfaces of teeth. More particularly, the invention relates to modified orthodontic brackets, light curing assemblies and bonding methods that provide enhanced bond strength between the bracket and the tooth and especially beneath a central portion of the bracket base.

2. Description of the Related Art

Orthodontic treatment involves movement of the teeth toward desired positions for correct occlusion. During treatment, tiny slotted orthodontic appliances known as brackets are connected to the teeth, and an archwire is placed in the slot of each bracket. The archwire forms a track to guide movement of the teeth to orthodontically correct positions.

Many commercially available orthodontic brackets are adapted to be directly bonded to the surface of the patient's teeth by means of an orthodontic bonding adhesive. Some adhesives such as CONCISE brand adhesive (from 3M Unitek) are supplied as two initially separate components that, once mixed together, are self-curing. Such two-component adhesives, however, have only a limited "working time" during which the orthodontist can transfer the adhesive to the bracket base, place the bracket on the tooth and shift the bracket to a particular desired position on the tooth before the adhesive begins to harden.

Other adhesives, such as TRANSBOND brand adhesive (also from 3M Unitek) are light-curable and begin to cure once a source of light is directed toward the adhesive. Light-curable adhesives are preferred by many orthodontists because the length of the "working time" can be chosen as needed. In use, the bracket can be carefully placed on the patient's tooth and shifted as desired until the orthodontist is satisfied with the position of the bracket. Advantageously, the adhesive does not harden until a source of light is directed toward the adhesive.

Many attempts over the years to increase the strength of the bond between the bracket and the tooth. Some brackets, for example, have an outer base surface that is roughened, scribed or dimpled, while other brackets have a base surface that includes one or more layers of irregularly-shaped fragments or spherical particles. Such base surfaces present an increased surface area available for contact with the adhesive in order to improve the strength of the bond between the bracket and the tooth.

Certain brackets have bases that present undercut regions. Undercuts in the base enable the adhesive, once hardened, to form a mechanical interlock with the bracket. For example, the irregularly-shaped fragments or spherical particles mentioned above may present undercut regions. As another example, the bases of some brackets have a fine mesh metal "screen" or pad that provides a mechanical interlock when embedded into cured adhesive. Other brackets, such as that shown in U.S. Design Pat. No. 290,040, have a series of undercut grooves that provide a mechanical interlock with hardened adhesive. U.S. Pat. Nos. 4,094,068 and 5,435,720 describe brackets having bases with peripheral holes or notches that enable the adhesive to flow through and produce an enlarged head that serves to improve retention of the bracket on the tooth.

However, there is a continuing need in the art to improve the strength of the bond between certain types of brackets and the patient's teeth in order to avoid spontaneous, unintentional debonding of the bracket during treatment. In some instances, the bond may not have sufficient strength to retain the bracket on the tooth when the bracket is subjected to relatively large forces, as when the patient bites into a relatively hard food object. In other instances, the bracket may debond from forces exerted by the archwire, by orthodontic auxiliaries or by attachments coupled to the bracket. Premature debonding of orthodontic brackets represents a nuisance to both the orthodontist and the patient that is best avoided, since the patient normally must return to the orthodontist for rebonding of the detached bracket or replacement with a new bracket in order to resume treatment.

Moreover, recent efforts have been directed toward increasing the bond strength when a light-curable bonding adhesive is used in conjunction with a metal bracket. When light-curable adhesive is used with a bracket made of translucent or transparent plastic, ceramic or other material, the light from the curing apparatus typically passes through the bracket and cures most, if not all, of the adhesive between the bracket base and the tooth. However, metal brackets substantially block the passage of light to the central portion of the bracket base, with the result that adhesive adjacent the central portion remains uncured. Often, the curing light is directed toward the adhesive along two or more edges of the base of metal brackets, but such practice may not cure a sufficient amount of adhesive to a degree necessary to preclude unintentional debonding of the bracket when the bracket is subjected to a relatively large force.

Another difficulty that is sometimes encountered in orthodontic bracket bonding procedures pertains to removal of excess adhesive following placement of the bracket but prior to the time that the adhesive has hardened. In many bonding procedures, the bracket is carefully positioned in a selected location and then pressure is applied to the bracket to firmly seat the bracket in the adhesive. Often, the orthodontist will choose to apply an excess amount of adhesive to the bracket base prior to seating to insure that the entire surface of the bracket base is in contact with adhesive and to reduce the possibility of air bubbles or voids between the bracket and the tooth where adhesive is not present. During seating, the excess adhesive is extruded from beneath the bracket base and onto areas of the patient's tooth adjacent the periphery of the bracket base. A dental explorer or other tool is then used to pick up and remove the extruded adhesive from the tooth's surface.

During removal of excess adhesive, however, the explorer may bump against the bracket and shift the bracket slightly from its intended position. In such instances, it is often inadvisable to simply shift the bracket back to its initial location because insufficient adhesive may remain beneath the bracket base for satisfactory bonding and voids may be established. Instead, recommended practice typically involves removal of the bracket and adhesive from the tooth, placing an additional quantity of adhesive on the bracket base, repositioning and reseating the bracket on the tooth and removal of the newly extruded adhesive, a procedure that is somewhat time-consuming at best.

SUMMARY OF THE INVENTION

The present invention overcomes the problems noted above in connection with conventional brackets, light-curing units and procedures by provision of improved methods and apparatus for bonding a portion of the adhesive that is directly between a central portion of the bracket base and the patient's tooth. If desired, the methods and apparatus as described herein may be advantageously used to temporarily secure the bracket to the tooth without curing of the adhesive that has been extruded from peripheral edges of the bracket base during seating of the bracket. Once the bracket is temporarily secured to the tooth in such a manner, the excess, extruded adhesive can be easily removed with a dental explorer or other tool and yet the cured portion of the adhesive will prevent movement of the bracket even when unintentionally bumped by the explorer. Following removal of the extruded adhesive, the curing unit can be used to cure portions of the adhesive between peripheral edges of the bracket base and the tooth in order to increase the strength of the adhesive bond to a value useful for orthodontic treatment.

More particularly, the invention in one aspect concerns the combination of an orthodontic bracket and a curing light assembly. The combination includes an orthodontic bracket having a base with an outer surface for direct bonding to a tooth, wherein the base includes a central portion with at least one opening. The bracket also includes a body extending from the base in a direction away from the outer surface. The bracket also includes at least one tiewing extending outwardly from a body, and the slot next to the tiewing(s) for receiving an archwire. The body includes a central section having a passage aligned with the opening(s) of the base. The combination also includes a curing light assembly having a housing with an outer end portion of a size sufficient for reception in the passage of the bracket body. The curing light assembly includes a source of light connected to the housing for emitting light from the outer end portion in order to cure bonding adhesive in contact with the central portion of the bracket base when the outer end portion of the housing is received in the passage.

Another aspect of the invention relates to an orthodontic bracket that comprises a base having an outer surface for direct bonding to a tooth, wherein the base includes a central portion with at least one opening. The bracket also includes a body extending from the base in a direction away from the outer surface. The body includes a central section having a passage. At least one tiewing extends outwardly from the body, and a slot is next to the tiewing(s) for receiving an archwire. The body includes a passage that is aligned with the opening(s) of the base for receiving a source of light to cure light-curable bonding adhesive in contact with the central portion of the base.

An additional aspect of the invention is directed toward an orthodontic curing light assembly that comprises an elongated housing having an outer end portion of a size sufficiently small to fit within a passage of an orthodontic bracket, and a source of light connected to the housing. The source of light is operable to direct light in a direction along an axis generally parallel to the longitudinal axis of the housing. At least one tab is coupled to the housing and extends outwardly from the housing in a direction generally perpendicular to the longitudinal axis of the housing for limiting the depth of insertion of the housing in the passage of the bracket.

The invention also relates to an orthodontic curing light assembly that comprises a housing with an outer end portion and a source of light connected to the housing. The source of light is operable to emit light in a direction away from the outer end portion. The assembly also includes a coupler for detachably connecting the outer end portion to an orthodontic bracket.

A further aspect of the invention concerns a method of bonding an orthodontic bracket to a tooth. The method comprises the steps of providing an orthodontic bracket having a bracket body that is opaque to the passage of actinic radiation, and placing the orthodontic bracket on a surface of the tooth and in contact with a quantity of light-curable adhesive located between the bracket and the tooth. The method also includes the step of directing light through a passage extending through a central section of the bracket body in order to cure adhesive located between the central section and the tooth. Light is also directed toward a periphery of the bracket in order to cure remaining portions of the adhesive.

The invention is particularly advantageous when used in connection with brackets made of an opaque material such as stainless steel or other metals, since the passage in the bracket permits light to reach adhesive beneath a central portion of the bracket base that would otherwise remain substantially uncured. Bond strength between the bracket and the tooth is increased as a result, and the likelihood of unintentional, spontaneous debonding of the bracket during the course of treatment is significantly reduced.

Other aspects and advantages of the invention will become apparent after a review of the detailed description that follows along with the accompanying drawings.

DETAILED DESCRIPTION OF THE PREFERRED EMBODIMENTS

An orthodontic bracket constructed in accordance with the principles of the present invention is designated broadly by the numeral 20 in FIGS. 1–4 and 6–11. With reference initially to FIGS. 1–4, the bracket 20 includes a base 22 having an outer surface with a certain concave shape that is adapted for direct bonding to a particular tooth. Preferably, the concave shape has a compound contour that matches the convex outer surface of the tooth.

Figure 1:
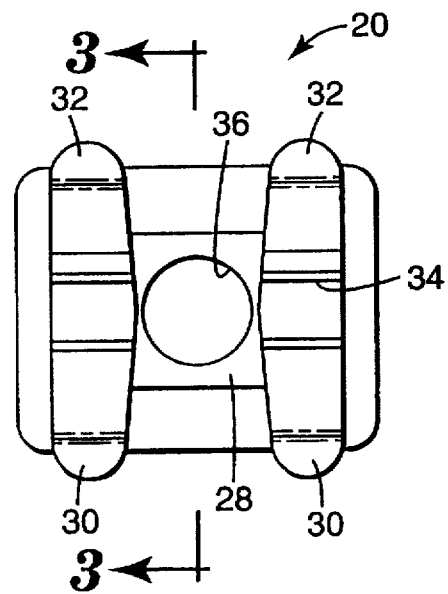
FIG. 1 is a front elevational view of an orthodontic bracket constructed in accordance with the principles of one aspect of the present invention, looking toward a buccal-labial side of the bracket.
Figure 3:
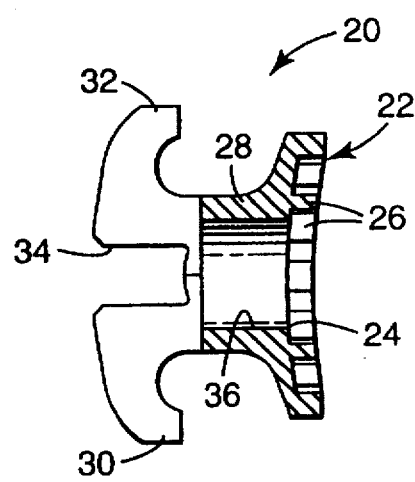
FIG. 3 is a side cross-sectional view of the bracket illustrated in FIGS. 1–2 and taken along lines 3—3 of FIG. 1.
Figure 2:
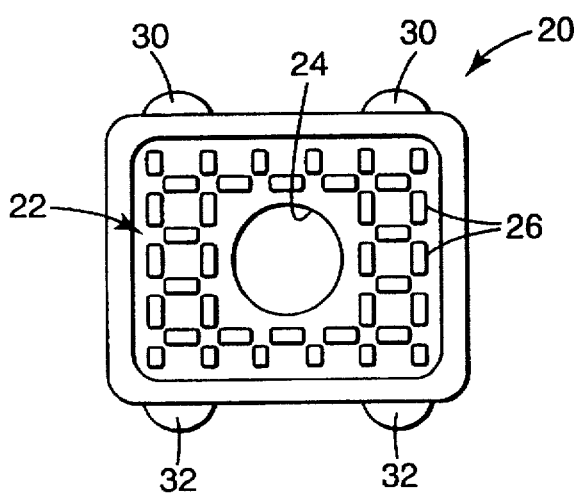
FIG. 2 is a rear elevational view of the bracket shown in FIG. 1, looking toward a tooth-facing base surface of the bracket.

The base 22 includes a central portion having a circular opening 24 (FIGS. 2–3). Additionally, the base 22 includes a series of upstanding pegs 26 that surround the opening 24. Although not shown in detail in the drawings, the pegs 26 preferably have outer ends that are peened over during a tumbling process to present mushroom-shaped heads that establish a mechanical interlock with an orthodontic bonding adhesive once the adhesive has hardened.

The bracket 20 also includes a body 28 that extends from the base 22 in a direction away from the outer surface of the base 22. In the particular embodiment shown in FIGS. 1 and 3–4, the mesial-distal length of the body 28 (i.e., in a direction extending between mesial and distal sides of the body 28) is less than the mesial-distal length of the base 22. Moreover, the occlusal-gingival height of the body 28 (i.e., in a direction between occlusal and gingival sides of the body 28) is less than the occlusal-gingival height of the base 22.

The bracket 20 also includes a pair of spaced apart occlusal tiewings 30 that extend away from the body 28 in a buccal-labial direction (i.e., in a direction toward the patient's lips or cheeks) as well as in an occlusal direction (i.e., in a direction toward the outer ends or tips of the patient's teeth). In addition, the bracket 20 includes two spaced apart gingival tiewings 32 that extend in a buccal-labial direction as well as in a gingival direction (i.e., in a direction toward the patient's gums or gingiva). The tiewings 30, 32 are integrally connected to the body 28, which in turn is preferably integrally interconnected to the base 22.

An archwire slot 34 extends in a generally mesial-distal direction across the bracket 20. The archwire slot 34 is comprised of a mesial slot portion located between the occlusal tiewing 30 and the gingival tiewing 32 which are connected to a mesial side of the body 28, and a distal slot portion located between the occlusal tiewing 30 and the gingival tiewing 32 which are connected to the distal side of the body 28. As shown for example in FIG. 3, the bottom of the archwire slot 34 (i.e., the wall of the archwire slot 34 that is closest to the base 22 of the bracket 20) is slightly spaced in a buccal-labial direction from a buccal-labial side of the body 28.

The body 28 includes a central section located between the mesial side of the body 28 (which is connected to the mesial pair of tiewings 30, 32) and the distal side of the body 28 (which is connected to the distal pair of tiewings 30, 32).

The central section of the body 28 includes an enclosed, central passage 36 that is open on both ends and preferably has a cylindrical sidewall. The passage 36 extends from the buccal-labial side of the body 28 to the lingual side of the body 28 (i.e., in a direction toward the patient's cheeks) and is aligned with the circular opening 24 of the bracket base 22.

Preferably, the passage 36 is aligned with the opening 24 in both an occlusal-gingival direction and a mesial-distal direction, and in the embodiment shown the circular opening 24 has the same diameter and is located at the lingual end of the passage 36. The central axis of the passage 36, when extended, passes through the archwire slot 34 and preferably passes through the middle of the archwire slot 34 when considered in an occlusal-gingival direction. Preferably, but not necessarily, the central axis of the passage 36 is parallel to the occlusal and gingival walls defining the archwire slot 34.

Figure 5:
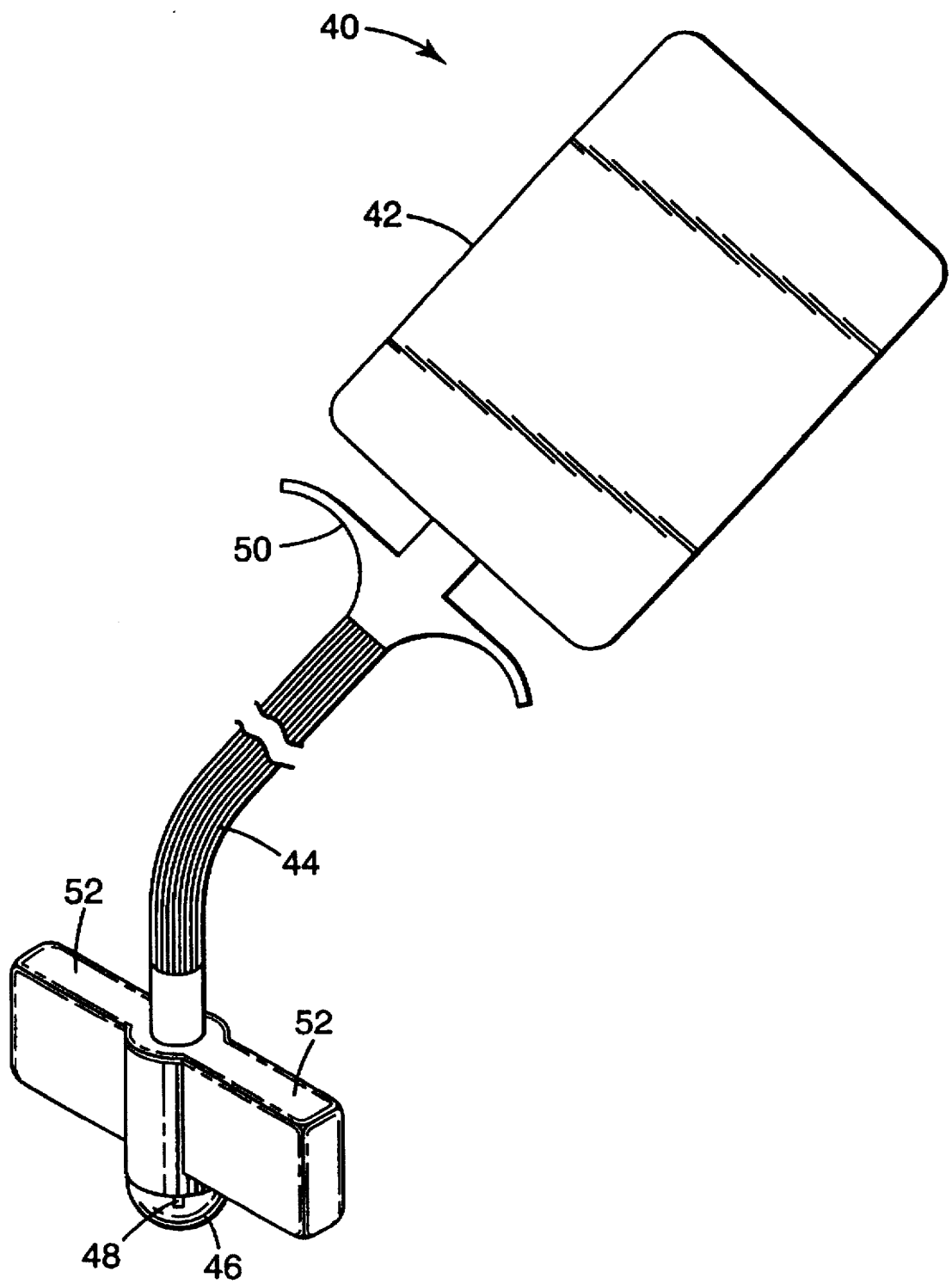
FIG. 5 is a perspective view (not to scale) of a curing light assembly according to another aspect of the invention and adapted for use with the bracket depicted in FIGS. 1–4.
Figure 6:
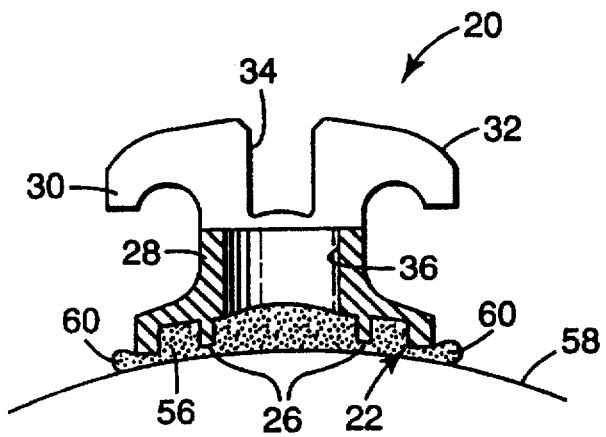
FIG. 6 is a view somewhat similar to FIG. 3, except that the bracket is depicted as placed on a tooth and in contact with a quantity of bonding adhesive.

A curing light assembly according to another aspect of the invention is broadly designated by the numeral 40 and is shown in FIGS. 5 and 7–11. As depicted in FIG. 5, the assembly 40 in this embodiment includes a case 42 that contains a portable power source such as a rechargeable battery. The case 49 is connected to an elongated housing 44.

The housing 44 preferably is constructed so that its configuration is repositionable and can be changed to any one of a number of different self-supporting configurations. For example, the housing 44 may have a straight longitudinal axis, or be repositioned to have a curved longitudinal axis in any one of a number of different arcs. The housing 44 may be constructed by providing an interconnected series of annular sections similar to those used for gooseneck lamps and the like.

The housing 44 has an outer end portion 46 that contains a source of light. Preferably, the source of light is a solid state light emitter 48 (FIG. 5 only) such as a light emitting diode. As used herein, the phrase "solid state light emitter" means any device that converts electric energy into electromagnetic radiation through the recombination of holes and electrons. Examples of solid state light emitters include semi-conductor light emitting diodes, semi-conductor laser diodes, polymer light emitting diodes and electroluminescent devices (i.e., devices that convert electric energy to light by a solid phosphor subjected to an alternating electric field).

Optionally, the outer end portion 46 may comprise a focusing lens for the emitter 48, such as the dome-shaped lens that covers commonly available light emitting diodes. The lens preferably is shaped to direct a substantial majority of the light emitted from the emitter in a forward direction that is generally parallel with the longitudinal axis of the housing 44.

The emitter 48 is connected by a pair of wires (not shown) that extend within the housing 44 to the battery power source within the case 42. A spring-loaded finger switch 50 is movably connected to the case 42 and is electrically connected to one of the wires extending between the emitter 48 and the power source. When the switch 50 is depressed, the switch 50 closes the circuit and enables the emitter 48 to receive current from the power source.

The outer end portion 46 is of a size sufficiently small to fit within the confines of the passage 36. For example, if the passage 36 has a diameter of 0.04 inch (1 mm), and the outer end portion 46 has the shape of a hemisphere, the diameter of the hemisphere is 0.03 inch (0.75 mm). The hemisphere has a diameter that is preferably just slightly less than the diameter of the passage 36.

Optionally, the outer end portion 46 is provided with a means for readily detaching from any orthodontic adhesive that it contacts. Such means could comprise, for example, a release coating such as a silicone polymer or a hard coating similar to coatings used for coating eyeglass lenses.

The curing light assembly also includes at least one tab 52 that is coupled to the housing 44. In the embodiment shown, a pair of tabs 52 are provided and extend outwardly in opposite directions away from each other as well as from the housing 44. The tabs 52 are connected to a central cylindrical member that is located directly adjacent the outer end portion 46. The housing 44 extends through a bore that passes through the center of the cylindrical member.

The tabs 52 have a transverse cross-sectional configuration that is complemental to the cross-sectional configuration of the archwire slot 34. More particularly, the tabs 52 have a width that is just slightly smaller than the occlusal-gingival width of the archwire slot 34. Commonly, orthodontic brackets are available with rectangular archwire slots having nominal occlusal-gingival dimensions of 0.018 inch (0.46 mm) and 0.022 inch (0.56 mm). The width of the tabs 52, similar to the occlusal-gingival dimensions of mating archwires, is slightly smaller than such corresponding archwire slot dimensions to enable the tabs to be readily inserted or removed from the archwire slot 34 without undue free play or "slop".

Preferably, the distance between the outer ends of the tabs 52 is equal or slightly larger than the distance between the mesial and distal ends of the archwire slot of the widest expected bracket, so that good control over movement of the bracket can be achieved when desired.

Optionally, the tabs 52 including the central cylindrical member are detachably received on the housing 44 and held in place by friction or by other structure such as a latch. As a result, the tabs 52 may be removed from the housing 44 when desired and replaced with other tabs, such as tabs that have a different occlusal-gingival dimension to match other brackets. Preferably, the structure coupling the tabs 52 to the housing 44 prevents relative rotation of the tabs 52 in an arc about the longitudinal axis of the housing 44, so that the housing 44 may be turned in order to control movement and ultimate placement of the bracket 20. To provide for removal of the tabs 52, the housing 44 may be detachably connected to the case 42, or alternatively the outer end portion 46 may be detachably connected to the remainder of the housing 44.

Optionally, the tabs 52 have a color that contrasts with the material of the bracket 20 to facilitate visual observation of the tabs 52. For example, the tabs 52 may be provided with a black color or a black coating to enhance the contrast between the tabs 52 and the metallic color of the bracket 20. Such color contrast enables the orthodontist to easily align the tabs 52 and hence align the archwire slot 34 with the desired occlusal plane of the patient as the bracket 20 is moved to its final intended position on the patient's tooth.

One method of using the curing light assembly 40 with the bracket 20 is illustrated by the steps shown in FIGS. 6–11. First, a quantity of light curable bonding adhesive 56 (such as TRANSBOND brand adhesive from 3M Unitek) is placed on the bracket base 22 in contact with the pegs 26 as well as over the opening 24. Next, the bracket 20 with the adhesive 56 is placed onto the exterior surface of a patient's tooth 58.

Preferably, the quantity of adhesive 56 initially placed on the base 20 is greater than the quantity of adhesive 56 that is needed to ultimately bond the bracket 20 to the tooth 58. As a consequence, as the bracket 20 is pushed toward the tooth 58 until firmly seated, portions 60 of the adhesive 56 are extruded from the four peripheral sides of the bracket base 22. The shifting movement and extrusion of the adhesive 56 reduces the likelihood of gaps or voids in the adhesive 56 in regions between the bracket base 22 and the surface of the tooth 58.

Figure 7:
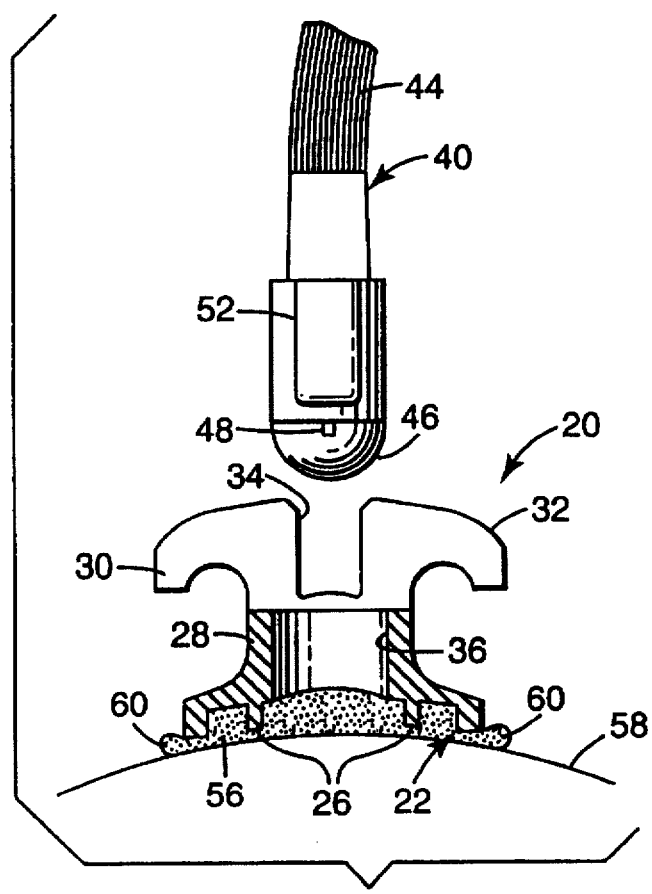
FIG. 7 is a view somewhat similar to FIG. 6 and additionally illustrating the curing light assembly shown in FIG. 5 as it is moved toward a passage of the bracket.
Figure 8:
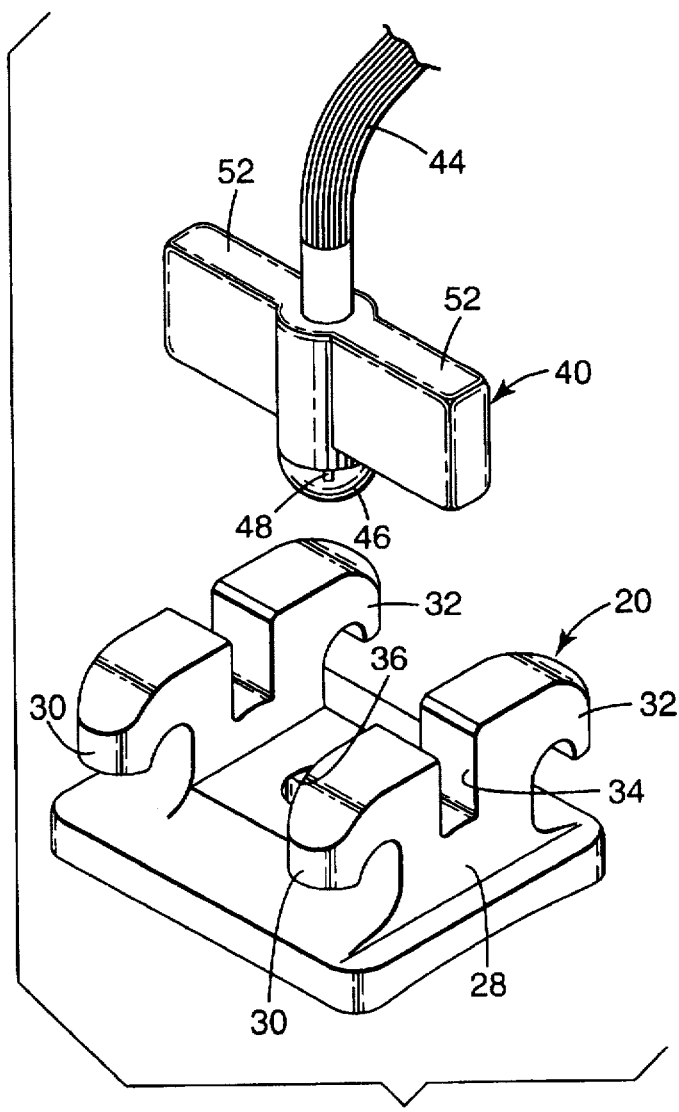
FIG. 8 is a perspective view of the bracket and curing light assembly shown in FIG. 7.

Next, and as illustrated in FIGS. 7–8, the housing 44 of the curing light assembly 40 is moved toward the bracket 20 in the direction shown by the arrow in FIG. 7 and in such a manner that the central, longitudinal axis of the housing 44 including the outer end portion 46 is collinear with the central longitudinal axis of the passage 36. In addition, the housing 44 is rotated as needed about its longitudinal axis in order to align the tabs 52 with the archwire slot 34. The curing light assembly 40 continues to move toward the bracket 20 until the outer end portion 46 enters the passage 36 and the tabs 52 are received in the archwire slot 34 in the coupled-together manner shown in FIGS. 9 and 10.

Next, the orthodontist shifts the bracket 20 relative to the tooth 58 slightly as needed to place the bracket 20 in the precise, desired position on the tooth 58. For example, the orthodontist may shift the bracket 20 until the archwire slot 34 is aligned with the occlusal plane of the patient and the edges of the tiewings 30, 32 are aligned with the longitudinal axis of the tooth 58. The positioning of the bracket 20, including movements in occlusal-gingival directions, mesial-distal directions or rotational movements about the central axis of the passage 36 are carried out by moving the housing 44 relative to the tooth 58, inasmuch as the tabs 52 and the outer end portion 46 serve to control movement of the bracket 20. The tabs 52 also serve as a coupler for connecting the outer end portion 46 to the bracket 20.

In some instances, the configuration of the housing 44 may need to be changed in order to facilitate placement of certain brackets. For example, the orthodontist may prefer to bend the housing 44 to a curved configuration such as that shown in FIG. 5 when the curing light assembly 40 is used to bond brackets to molar teeth or bicuspid teeth. Alternatively, the orthodontist may prefer to change the configuration of the housing 44 to a straight configuration in instances where the bracket 20 is to be placed on relatively accessible teeth such as the patient's central or lateral teeth.

Figure 9:
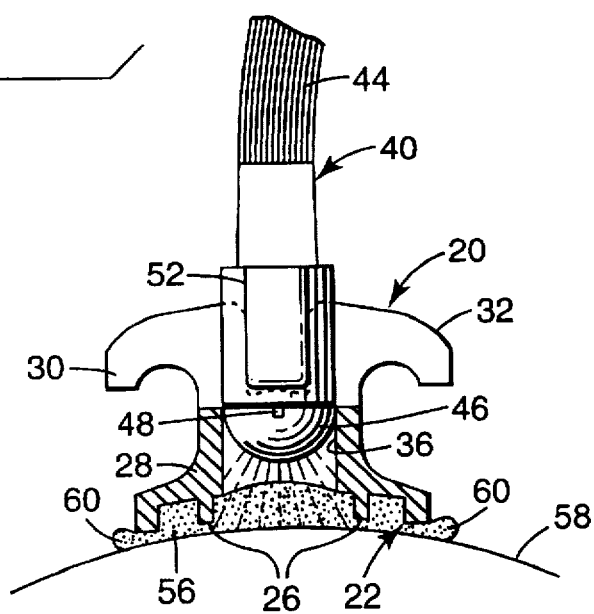
FIG. 9 is a view somewhat similar to FIG. 7 except that the curing light assembly has been fully received in the passage of the bracket to initially allow the orthodontist to precisely position the bracket on the tooth, and wherein the light has been subsequently activated to cure a portion of the adhesive directly beneath the passage.
Figure 10:
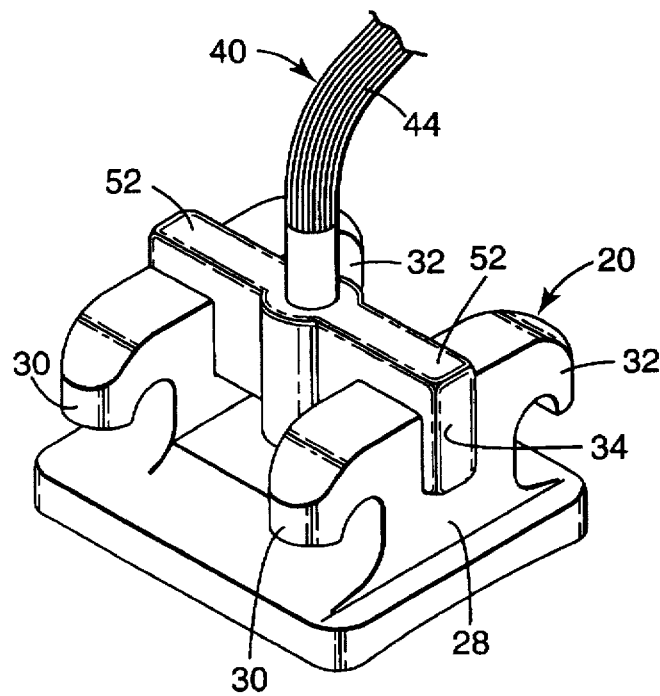
FIG. 10 is a perspective view of the bracket and curing light assembly illustrated in FIG. 9.

Next, and as depicted in FIG. 9, the solid state emitter 48 is energized by depressing the switch 50. Light emitted from the emitter 48 reaches a portion of the adhesive (designated 62 in FIG. 11) that is located between the central section of the bracket body 28 and the tooth 58. The adhesive portion 62 cures and provides a "tack" bond that temporarily secures the bracket 20 to the tooth 58.

Figure 11:
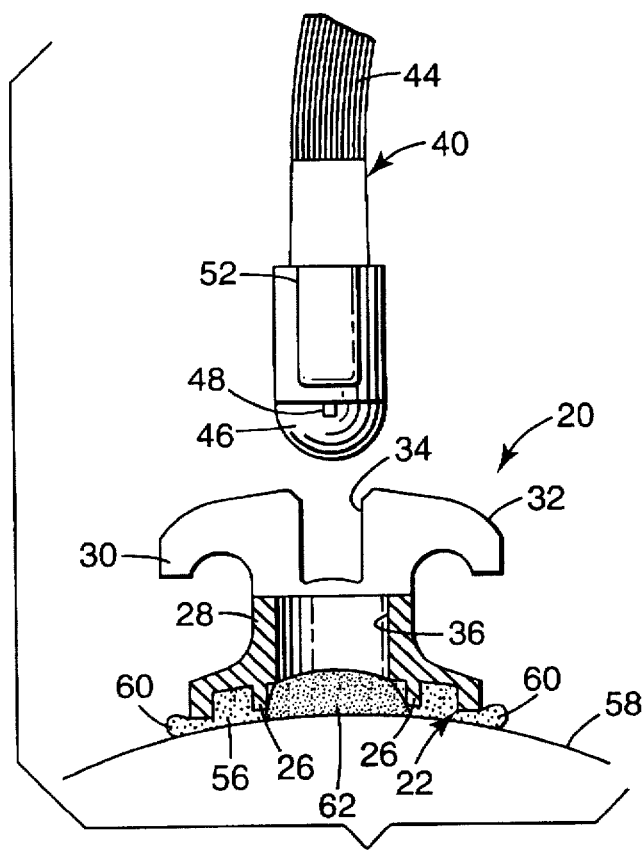
FIG. 11 is a view somewhat similar to FIG. 9, except that adhesive beneath the passage has cured and the curing light assembly has been removed from the passage.

Next, and as indicated in FIG. 11, the curing light assembly 40 is removed from the bracket 20 by moving the housing 44 away from the bracket body 28 in the direction of the arrow until the outer end portion 46 is removed from the passage 36 and the tabs 52 are removed from the archwire slot 34. Preferably, the orthodontist then uses a dental explorer or other tool to remove the extruded adhesive portions 60 from the tooth 58 adjacent the four peripheral edges of the bracket base 22. The cured adhesive portion 62 couples the bracket 20 to the tooth 58 with sufficient force to normally retain the bracket 20 in place if, for example, the bracket 20 is accidentally bumped or disturbed during the cleaning procedure. However, the use of light in the passage 34 does not substantially cure the adhesive 56 other than the cured portion 62, and thus the extruded adhesive portions 60 are not hardened and can be readily removed from the surface of the tooth 58.

Subsequently, remaining portions of the adhesive 56 between the bracket base 22 and the tooth 58 are cured by directing light toward peripheral edges of the bracket base 22. If desired, the curing light assembly 40 can be used when uncoupled from the bracket 20 for such peripheral curing, or another curing light assembly, possibly emitting a greater intensity of light, can be used. Preferably, the light is directed toward at least two of the four peripheral edges of the base 22 such as the mesial and distal side edge of the base 22.

As an alternative procedure, the curing light assembly 40 may be used to firmly press the bracket 20 onto the tooth 58 in addition to controlling the movement of the bracket 20. If desired, the bracket 20 may be coupled to the tabs 52 before the bracket 20 is placed on the surface of the tooth 58.

One significant advantage of the invention is that the orthodontist may use adhesives that are less viscous than conventional orthodontic adhesives used for direct bonding. Less viscous adhesives flow around the undercuts and other microstructure of the bracket base 22 more readily than thicker, more viscous adhesives and thus may provide higher bond strengths than such thicker adhesives. Drift of the bracket 20 on the tooth 58 before the adhesive is cured can be avoided because the curing light assembly 40 controls movement of the bracket 20 until tack bonded. In the past, however, relatively thick adhesives have been generally preferred because such adhesives hinder drift of the bracket 20 after placement on the tooth 58.

Preferably, the solid state light emitter 48 is a blue light emitting diode that emits light having a wavelength substantially in the range of about 413 nanometers to about 535 nanometers, and preferably emits the greatest intensity at a wavelength of about 450 nanometers. Suitable blue light emitting diodes include no. NLPB 500 from Nichia Chemical Industries, Ltd. Other wavelengths are also possible. The outer hemispherical lens of the LED is preferably sculpted to fit within the passage 36 and to direct the majority of its light along the longitudinal axis of the passage 36. Preferably, the light emitted by the emitter 48 in the passage 36 is of an intensity sufficient to cure the adhesive portion 62 in less than about 10 seconds, and more preferably in less than about 4 seconds.

Figure 12:
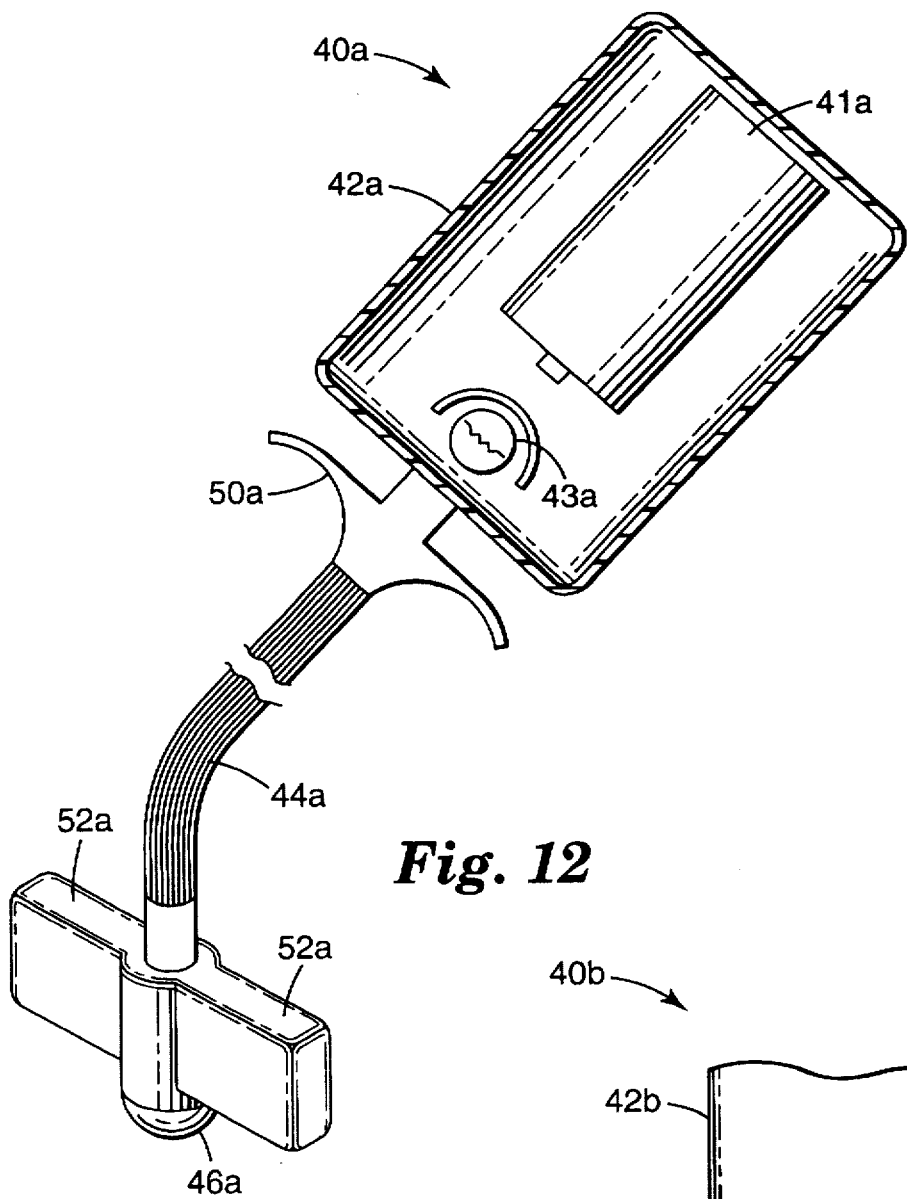
FIG. 12 is a perspective view (not to scale) of a light curing assembly according to another embodiment of the invention.

A second embodiment of a curing light assembly 40a according to another aspect of the invention is shown in FIG. 12. The assembly 40a includes a case 42a that in this instance includes a source of light such as a bulb 43a. Alternatively, a single solid state light emitter or a cluster of solid state light emitters (such as the blue light emitting diodes mentioned above) may be employed in place of the bulb 43a.

The case 42a also contains a source of power comprising a battery 41a that is electrically connected to the bulb 43a. A spring loaded finger switch 50a is movably connected to the case 42a. When the switch 50a is depressed, the battery 41a energizes the bulb 43a.

The assembly 40a also includes an elongated housing 44a that, in this instance, comprises a bundle of optical fibers. The bundle of optical fibers is somewhat flexible, and yet sufficiently stiff to retain a desired configuration when repositioned. The housing 44a in this embodiment is provided by the outer cladding of the fibers arranged around the periphery of the bundle. Alternatively, the bundle of optical fibers may be received inside of a flexible housing (such as the gooseneck mentioned above). As another alternative, a single optical fiber may be used, and in such case the housing 44a may comprise the cladding of such fiber, or instead may comprise a separate, flexible tubular member surrounding such cladding.

The housing 44a includes an enlarged outer end portion 46a that preferably is provided with a release coating or other release means as mentioned above. In addition, a pair of tabs 52a are connected to the housing 44a directly adjacent the outer end portion 46a. The tabs 52a are identical to the tabs 52 described above.

Figure 13:
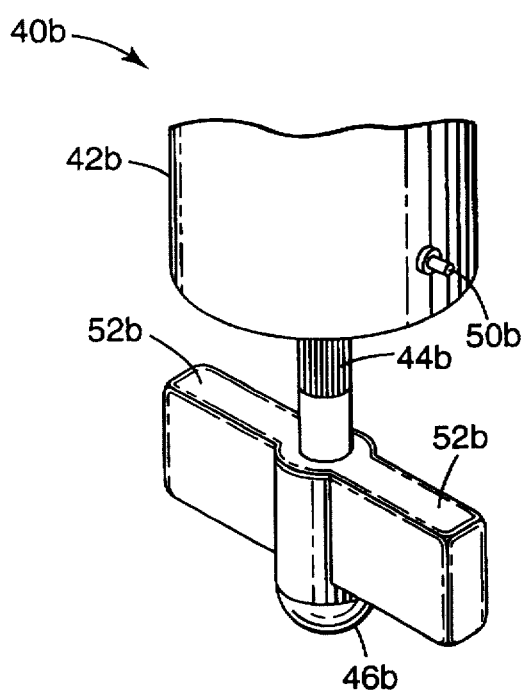
FIG. 13 is a fragmentary perspective view (not to scale) of a light curing assembly according to an additional embodiment of the invention.

A curing light assembly 40b according to another aspect of the invention is illustrated in FIG. 13. The assembly 40b includes a case 42b that, in this instance, is relatively small and is not illustrated to scale. The case 42b is just slightly larger in diameter than the diameter of a conventional "AAA" size battery that is contained within. Preferably, the case 42b has a shape similar to a pencil for easy grasping and manipulation. The case 42b is connected to and optionally is detachably connected to a relatively short housing 44b that has an outer end portion 46b.

A solid state light emitter (such as the blue light emitting diode mentioned above) is contained in the outer end portion 46b. Moreover, a pair of tabs 52b similar to the tabs 52 described above are connected to the housing 44b. A pushbutton switch 50b is mounted on the side of the case 42b to close the circuit and energize the solid state emitter when desired.

Figure 14:
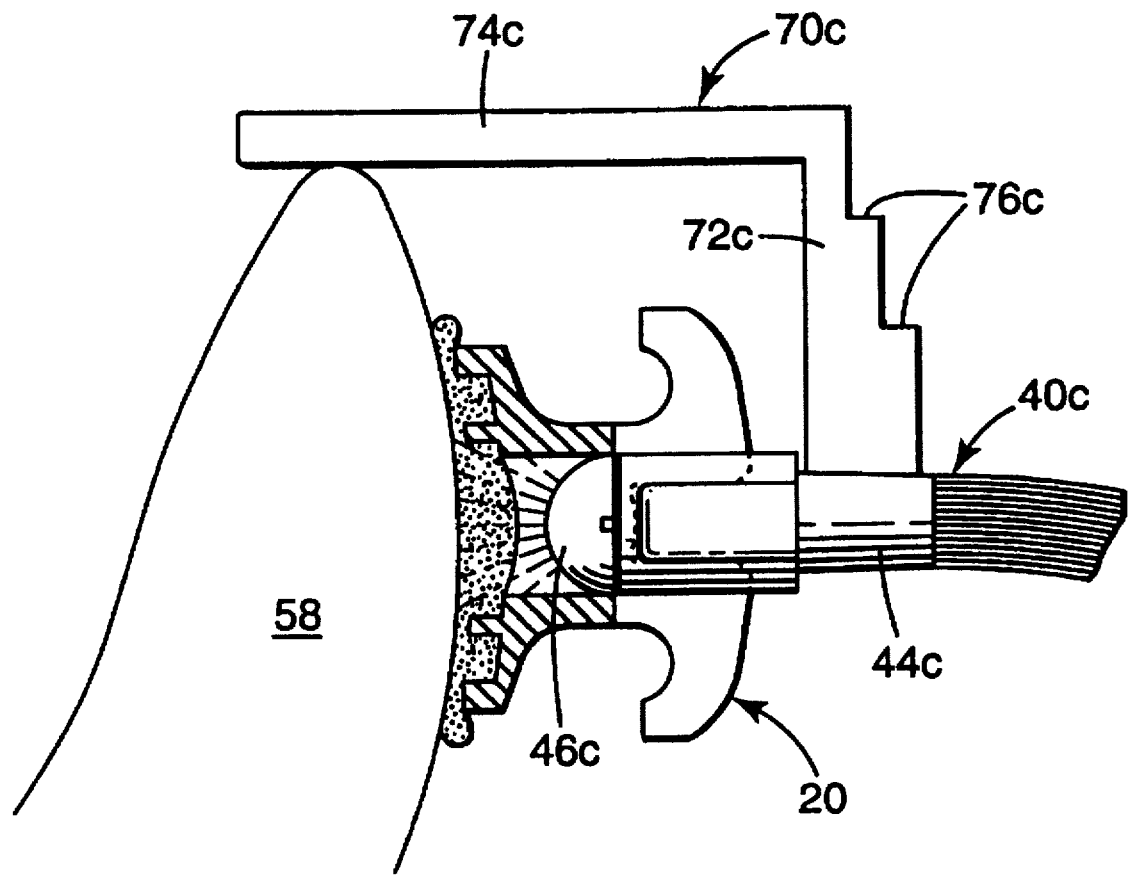
FIG. 14 is a fragmentary perspective view of a light curing assembly according to another embodiment of the invention along with a bracket and a quantity of bonding adhesive that have been placed on a tooth.

A curing light assembly 40c according to yet another embodiment of the invention is illustrated in FIG. 14. The assembly 40c is somewhat similar to the light curing assembly 40 shown in FIGS. 5 and 7-11, except that the assembly 40c includes a bracket height gauge 70c that is secured to a housing 44c. Optionally, the gauge 70c includes a sleeve that is slidably received on the housing 44c and held in place by friction, such that the gauge 70c can be removed from the housing 44c and replaced with a similar or different gauge when desired.

The gauge 70c has a generally L-shaped configuration with a first leg 72c and a second leg 74c that is integrally connected to the first leg 72c. The length of the first leg 72c is selected so that the archwire slot of the bracket 20 is located a certain distance in an occlusal-gingival direction from the outermost end (i.e., the occlusal or incisal edge) of the tooth 58 when an underside edge portion of the second leg 74c is in contact with the occlusal edge of the tooth 58. The gauge 70c therefore positions the bracket 20 at a predetermined height on the tooth 58 until such time that light is emitted from an outer end portion 46c of the assembly 40c to thereafter retain the bracket 20 in place.

Preferably, the first leg 72c includes a series of indicia to provide additional structure for determining the distance of the archwire slot of the bracket 20 from the occlusal edge of the tooth 58. In the embodiment shown, the indicia comprise a pair of edges or shoulders 76c that can be visually aligned, if desired, to the occlusal edge of the tooth in instances where it is desired to position the bracket 20 at a height on the tooth 58 other than the height provided when the second leg 74c is in contact with the occlusal edge. Other indicia, as well as an adjustable height gauge, are also possible.

Those skilled in the art may recognize that other modifications and variations of the embodiments described above in detail are also possible. For example, the batteries mentioned in the embodiments of the curing light assemblies described above may be replaced by a base unit that is connected to line current, with a pair of wires extending from the base unit to the housing which carries the source of light. Alternatively, a base unit connected to line current (such as ORTHOLUX XT brand curing light unit, catalog no. 704–804; from 3M Unitek) may include a light source that is optically and detachably connected by a single optical fiber or a bundle of optical fibers to the outer end portion of the housing. Moreover, the finger-operated switches 50, 50a or 50b may be replaced by a foot pedal switch or alternatively by a pressure sensitive switch that is operable to energize the emitter whenever sufficient pressure is applied to the bracket 20 by the curing light assembly 40, 40a, 40b, 40c.

Figure 2A:
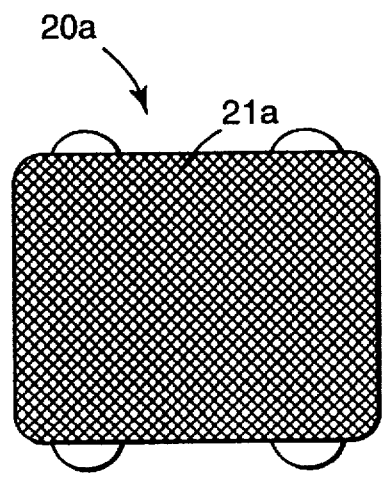
FIG. 2a is a view somewhat similar to FIG. 2 in accordance with another embodiment of the invention.
Figure 4:
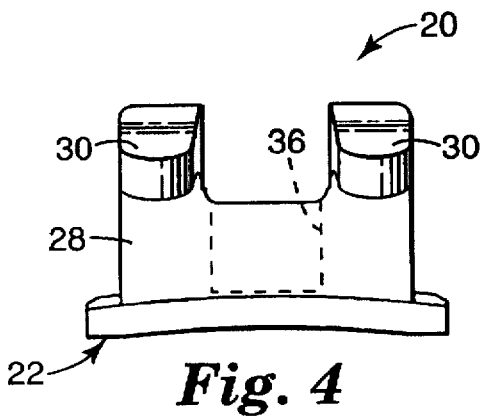
FIG. 4 is a side elevational view of the bracket shown in FIGS. 1–3 and looking toward an occlusal side of the bracket.

Additionally, the bracket 20 may be provided with a base having a mesh pad resembling fine wire mesh screening as shown for example in FIG. 2a by a bracket 20a having mesh pad 21a. If the mesh pad includes a layer of metallic foil bonded to the mesh screening, the foil is provided with one or more holes which would then serve as the opening of the base.

Brackets made of materials other than metallic materials may also be employed. For example, the bracket may be made of a transparent, translucent or opaque plastic or ceramic material. If the bracket is made of a material that transmits light, the intensity of light emitted by the curing light assembly is preferably relatively low. Such lower intensity is sufficient to cure the adhesive directly beneath the central section of the bracket body, but insufficient to cure adhesive near the peripheral edges of the bracket base so that extruded adhesive can be removed from the tooth surface with ease.

Brackets having archwire slot liners may also be used in connection with the present invention. Suitable brackets with liners are described, for example, in U.S. Pat. Nos. 5,380,196 and 5,366,372. In such an instance, the liner would comprise part of the bracket body and would include a hole to provide a passage that is aligned with an opening in the bracket base so that light can pass to adhesive beneath a central portion of the bracket base.

The invention may also be used with indirect bonding procedures. In an indirect bonding procedure, a set of the brackets is temporarily tack bonded in a laboratory to a model of the patient's teeth while each bracket is maintained in a certain position relative to each other and relative to the patient's model teeth. The set of brackets is then removed as a unit from the model and rebonded to the patient's actual teeth while their relative positions are maintained.

A number of other variations, modifications and additions are also possible and may be advantageously employed without departing from the spirit of the invention. Accordingly, the invention should not be deemed limited by the currently preferred embodiments that are described in detail above, but instead only by a fair scope of the claims that follow along with their equivalents.

We claim:

1. The combination of an orthodontic bracket and a curing light assembly comprising:

an orthodontic bracket having a base with an outer surface for direct bonding to a tooth, said base including a central portion with at least one opening, said bracket having a body extending from the base in a direction away from said outer surface, said bracket also including at least one tiewing extending outwardly from the body and the slot next to said at least one tiewing for receiving an archwire, said body including a central section having a passage aligned with said at least one opening; and a curing light assembly having a housing with an outer end portion of a size sufficient for reception in said passage, said curing light assembly including a source of light connected to said housing for emitting light from said outer end portion in order to cure bonding adhesive in contact with said central portion of said base when said outer end portion is received in said passage.

2. The combination of claim 1, wherein said curing light assembly includes at least one tab coupled to the housing and extending outwardly from the housing for limiting the depth of insertion of the housing in said passage.

3. The combination of claim 2, wherein said at least one tab is detachably coupled to said housing.

4. The combination of claim 1, wherein said housing comprises an optical fiber, and wherein said source of light is remote from said outer end portion of said housing.

5. The combination of claim 4, wherein said housing has a repositionable configuration.

6. The combination of claim 1, wherein said source of light is a solid state emitter.

7. The combination of claim 1, wherein said curing light assembly includes at least one tab that is coupled to said housing and is received in said archwire slot when said outer end portion of said housing is received in said passage.

8. The combination of claim 7, wherein said archwire slot has a certain length, and wherein said at least one tab extends along the entire length of said archwire slot.

9. The combination of claim 1, wherein said housing comprises one or more optical fibers.

10. The combination of claim 1, wherein said curing light assembly includes a gauge for determining the position of said bracket on the tooth.

11. The combination of claim 10, wherein said gauge is detachably connected to said housing.

12. The combination of claim 10, wherein said gauge has a generally L-shaped configuration with an outwardly extending leg for contact with an occlusal edge of the tooth.

13. The combination of claim 10, wherein said gauge includes a series of indicia for visual alignment with the tooth.

14. An orthodontic bracket comprising:

a base having an outer surface for direct bonding to a tooth, said base including a central portion with at least one opening;

a body extending from the base in a direction away from said outer surface;

at least one tiewing extending outwardly from said body; and a slot next to said at least one tiewing for receiving an archwire, said body including a passage extending through said body and aligned with said at least one opening for receiving a source of light to cure light-curable bonding adhesive in contact with said central portion of said base.

15. The bracket of claim 14, wherein said passage has a central reference axis that passes through said slot.

16. The bracket of claim 15, wherein said axis passes through approximately the center of said slot when considered in an occlusal-gingival direction.

17. The bracket of claim 14, wherein said passage is cylindrical.

18. The bracket of claim 14, wherein said base includes a mesh presenting a series of openings in said central portion.

19. An orthodontic curing light assembly comprising:

an elongated housing having an outer end portion of a size sufficiently small to fit within a passage of an orthodontic bracket;

a source of light connected to said housing and operable to direct light in a direction along an axis parallel to the longitudinal axis of said housing; and at least one tab coupled to said housing and extending outwardly from said housing in a direction generally perpendicular to the longitudinal axis of said housing for limiting the depth of insertion of said housing in the passage of the bracket.

20. The orthodontic curing light assembly of claim 19, wherein said at least one tab includes a pair of tabs extending outwardly in opposite directions from said housing.

21. The orthodontic curing light assembly of claim 19, wherein said at least one tab is detachably coupled to said housing.

22. The orthodontic curing light assembly of claim 19, wherein said housing has a repositionable configuration and can be changed from a configuration wherein said longitudinal axis is straight to a configuration wherein said longitudinal axis is curved.

23. The orthodontic curing light assembly of claim 22, wherein said housing includes at least one optical fiber.

24. The orthodontic curing light assembly of claim 19, wherein said source of light is a solid state emitter.

25. The orthodontic curing light assembly of claim 24, wherein said solid state emitter is directly adjacent said outer end portion of said housing.

26. The orthodontic curing light assembly of claim 24, wherein said solid state emitter emits blue light in the range of about 413 nanometers to about 535 nanometers.

27. The orthodontic curing light assembly of claim 19, and including a gauge for determining the position of said bracket on the tooth.

28. The orthodontic curing light assembly of claim 27, wherein said gauge is detachably connected to said housing.

29. The orthodontic curing light assembly of claim 27, wherein said gauge has a generally L-shaped configuration with an outwardly extending leg for contact with an occlusal edge of the tooth.

30. The orthodontic curing light assembly of claim 27, wherein said gauge includes a series of indicia for visual alignment with the tooth.

31. An orthodontic light curing assembly comprising a housing with an outer end portion;

a source of light connected to the housing and operable to emit light in a direction away from said outer end portion; and a coupler for detachably connecting said outer end portion to an orthodontic bracket.

32. The orthodontic curing light assembly of claim 31, wherein said coupler comprises a pair of outwardly extending tabs connected to said housing.

33. The orthodontic curing light assembly of claim 32, wherein said tabs are detachably coupled to said housing.

34. The orthodontic curing light assembly of claim 31, wherein said housing has a repositionable configuration and can be changed from a configuration wherein said longitudinal axis is straight to a configuration wherein said longitudinal axis is curved.

35. The orthodontic curing light assembly of claim 31, wherein said housing includes at least one optical fiber.

36. The orthodontic curing light assembly of claim 31, wherein said source of light is a solid state emitter.

37. The orthodontic curing light assembly of claim 31 and including a gauge for determining the position of said bracket on the tooth.

38. The orthodontic curing light assembly of claim 37, wherein said gauge is detachably connected to said housing.

39. The orthodontic curing light assembly of claim 37, wherein said gauge has a generally L-shaped configuration with an outwardly extending leg for contact with an occlusal edge of the tooth.

40. The orthodontic curing light assembly of claim 37, wherein said gauge includes a series of indicia for visual alignment with the tooth.

41. The method of bonding an orthodontic bracket to a tooth comprising the steps of:

providing an orthodontic bracket having a bracket body that is opaque to the passage of actinic radiation;

placing the orthodontic bracket on a surface of a tooth and in contact with a quantity of light-curable adhesive located between the bracket and the tooth;

directing light through a passage extending through a central section of a body of the bracket in order to cure adhesive located between the central section and the tooth; and directing light toward a periphery of the bracket in order to cure remaining portions of the adhesive.

42. The method of claim 41, wherein said step of placing the orthodontic bracket on a surface of a tooth includes the step of pressing the bracket toward the surface of the tooth with sufficient force to extrude adhesive from the periphery of the bracket, and wherein said method also includes the step of cleaning the extruded adhesive before said step of directing light toward the periphery of the bracket.

43. The method of claim 41, wherein said step of directing light through a passage includes the step of placing a housing of a curing light assembly at least partially in the passage.

44. The method of claim 43 and including the step of positioning the bracket on the surface of the tooth by moving the housing relative to the tooth.

45. The method of claim 41 and including the steps of connecting a light curing assembly to the bracket and contacting an occlusal edge of the tooth with a portion of the light curing assembly in order to position the bracket on the tooth.

46. The method of claim 41 and including the step of detachably connecting a light curing assembly having a source of light to the bracket.

* * * * *